(12) United States Patent
Krüger et al.

(10) Patent No.: US 6,929,006 B2
(45) Date of Patent: Aug. 16, 2005

(54) DEVICE AND PROCESS FOR METERING BREATHING GAS

(75) Inventors: Thomas Krüger, Reinfeld (DE); Hans-Georg Wahle, Reinfeld (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 0 days.

(21) Appl. No.: 10/983,343

(22) Filed: Nov. 8, 2004

(65) Prior Publication Data

US 2005/0133033 A1 Jun. 23, 2005

(30) Foreign Application Priority Data

Dec. 20, 2003 (DE) .................................. 103 60 229

(51) Int. Cl.[7] .......................... A61M 16/00; A62B 7/00; F16K 31/02
(52) U.S. Cl. ........................... 128/204.22; 128/200.24; 128/201.28; 128/203.28; 128/204.18; 128/204.21; 128/204.28; 128/204.29; 128/205.13; 128/205.14; 128/205.15; 128/205.17; 128/205.24
(58) Field of Search ....................... 128/200.24, 201.28, 128/203.28, 204.18, 204.21, 204.22, 204.28, 128/204.29, 205.13, 205.14, 205.15, 205.17, 128/205.24

(56) References Cited

U.S. PATENT DOCUMENTS

| | | | | |
|---|---|---|---|---|
| 3,017,881 A | * | 1/1962 | Smith ..................... | 128/205.13 |
| 3,556,097 A | * | 1/1971 | Wallace ................. | 128/202.23 |
| 4,067,328 A | * | 1/1978 | Manley .................. | 128/205.16 |
| 4,360,018 A | * | 11/1982 | Choksi ................... | 128/205.12 |
| 4,453,543 A | * | 6/1984 | Kohnke et al. ......... | 128/203.28 |
| 4,702,241 A | * | 10/1987 | Gravenstein et al. .. | 128/204.28 |
| 4,747,403 A | * | 5/1988 | Gluck et al. ........... | 128/204.21 |
| 4,791,922 A | * | 12/1988 | Lindsay-Scott et al. ..................... | 128/205.28 |
| 4,838,259 A | * | 6/1989 | Gluck et al. ........... | 128/204.21 |
| 4,883,051 A | * | 11/1989 | Westenskow et al. .. | 128/204.21 |
| 5,253,640 A | * | 10/1993 | Falb et al. ............. | 128/200.24 |
| 5,303,698 A | * | 4/1994 | Tobia et al. ........... | 128/204.21 |
| 5,398,675 A | * | 3/1995 | Henkin et al. ......... | 128/203.12 |
| 5,490,499 A | * | 2/1996 | Heinonen et al. ...... | 128/203.28 |

(Continued)

FOREIGN PATENT DOCUMENTS

DE        195 28 113 C2     9/2002

*Primary Examiner*—Henry Bennett
*Assistant Examiner*—Nihir Patel
(74) *Attorney, Agent, or Firm*—McGlew and Tuttle, PC

(57) ABSTRACT

A respirator with a tidal volume-measuring device (6) between a respiration bag (8) and a patient adapter (2) provides accurate metering of the tidal volume. The device includes a first pressure-measuring device (4) and a breathing gas interruptor (5) in series sequence between the patient adapter (2) and the tidal volume-measuring device (6). A second pressure-measuring device (7) is provided between the tidal volume-measuring device (6) and the respiration bag (8). A control unit (20) is connected with the tidal volume-measuring device (6) and the pressure-measuring devices (4, 7) and sends control signals in such a way that when a predetermined tidal volume is reached, the breathing gas interrupter (5) is switched to the closed position, and that the closed position is eliminated when the pressure $p_2$ measured with the second pressure-measuring means (7) has dropped below the pressure $p_1$ determined with the first pressure-measuring means (4).

3 Claims, 1 Drawing Sheet

U.S. PATENT DOCUMENTS

| | | | | | |
|---|---|---|---|---|---|
| 5,497,767 | A | * | 3/1996 | Olsson et al. | 128/205.13 |
| 5,507,280 | A | * | 4/1996 | Henkin et al. | 128/203.12 |
| 5,509,406 | A | * | 4/1996 | Kock et al. | 128/203.14 |
| 5,537,995 | A | * | 7/1996 | Ottestad | 128/204.28 |
| 5,540,220 | A | * | 7/1996 | Gropper et al. | 128/204.23 |
| 5,647,352 | A | * | 7/1997 | Niemi et al. | 128/204.28 |
| 5,664,563 | A | * | 9/1997 | Schroeder et al. | 128/204.25 |
| 5,676,133 | A | * | 10/1997 | Hickle et al. | 128/205.12 |
| 5,678,540 | A | * | 10/1997 | Kock et al. | 128/205.13 |
| 5,694,924 | A | * | 12/1997 | Cewers | 128/204.21 |
| 5,782,233 | A | * | 7/1998 | Niemi et al. | 128/202.22 |
| 5,795,787 | A | * | 8/1998 | Silkoff et al. | 436/116 |
| 5,810,002 | A | * | 9/1998 | Dittmann | 128/203.12 |
| 5,875,777 | A | * | 3/1999 | Eriksson | 128/204.21 |
| 5,878,744 | A | * | 3/1999 | Pfeiffer | 128/204.23 |
| 5,915,381 | A | * | 6/1999 | Nord | 128/204.23 |
| 5,931,159 | A | * | 8/1999 | Suzuki et al. | 128/204.18 |
| 5,957,130 | A | * | 9/1999 | Krahbichler et al. | 128/205.14 |
| 5,979,443 | A | * | 11/1999 | Dingley | 128/204.28 |
| 6,000,397 | A | * | 12/1999 | Skog | 128/204.22 |
| 6,035,851 | A | * | 3/2000 | Wallen | 128/202.22 |
| 6,119,686 | A | * | 9/2000 | Somerson et al. | 128/202.22 |
| 6,131,571 | A | * | 10/2000 | Lampotang et al. | 128/204.21 |
| 6,135,106 | A | * | 10/2000 | Dirks et al. | 128/204.23 |
| 6,213,120 | B1 | * | 4/2001 | Block et al. | 128/204.23 |
| 6,253,765 | B1 | * | 7/2001 | Hognelid et al. | 128/204.16 |
| 6,286,505 | B1 | * | 9/2001 | Psaros | 128/203.12 |
| 6,289,891 | B1 | * | 9/2001 | Cewers | 128/203.12 |
| 6,328,036 | B1 | * | 12/2001 | Emtell et al. | 128/205.14 |
| 6,345,538 | B1 | * | 2/2002 | Krahbichler et al. | 73/861.27 |
| 6,349,723 | B1 | * | 2/2002 | Kock | 128/203.28 |
| 6,422,237 | B1 | * | 7/2002 | Engel et al. | 128/204.21 |
| 6,523,538 | B1 | * | 2/2003 | Wikefeldt | 128/204.18 |
| 6,584,973 | B1 | * | 7/2003 | Biondi et al. | 128/204.21 |
| 6,601,583 | B2 | * | 8/2003 | Pessala et al. | 128/204.23 |
| 6,622,726 | B1 | * | 9/2003 | Du | 126/204.26 |
| 6,644,310 | B1 | * | 11/2003 | Delache et al. | 128/204.21 |
| 6,647,984 | B1 | * | 11/2003 | O'Dea | 128/207.16 |
| 6,648,832 | B2 | * | 11/2003 | Orr et al. | 600/532 |
| 6,651,652 | B1 | * | 11/2003 | Wård | 128/200.24 |
| 6,651,657 | B1 | * | 11/2003 | Manigel et al. | 128/204.21 |
| 6,668,829 | B2 | * | 12/2003 | Biondi et al. | 128/204.21 |
| 6,672,300 | B1 | * | 1/2004 | Grant | 128/204.26 |
| 6,679,259 | B2 | * | 1/2004 | Heesch | 128/204.26 |
| 6,718,978 | B2 | * | 4/2004 | Emtell | 128/204.28 |
| 6,761,166 | B2 | * | 7/2004 | Ahlmen et al. | 128/204.22 |

* cited by examiner

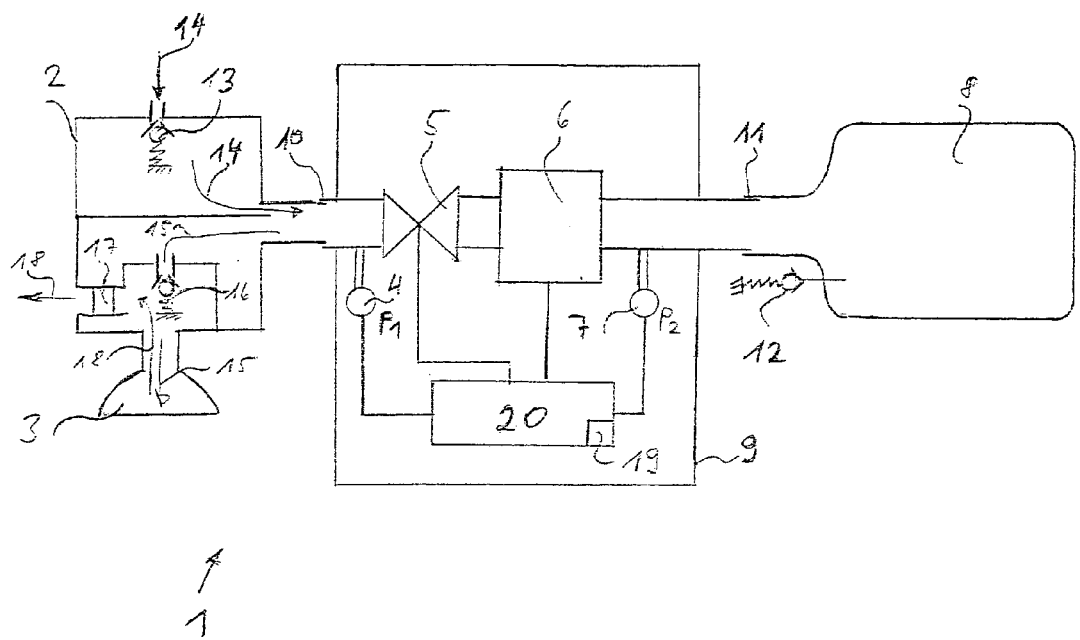

DEVICE AND PROCESS FOR METERING BREATHING GAS

CROSS REFERENCE TO RELATED APPLICATIONS

This application claims the benefit of priority under 35 U.S.C. § 119 of DE 103 60 229.1 filed Dec. 20, 2003, the entire contents of which are incorporated herein by reference.

FIELD OF THE INVENTION

The invention relates to respirators/ventilators (hereinafter respirators) generally and more particularly to manual respiration bags for the manual positive pressure respiration (ventilation) of premature baby patients to maintain ventilation.

BACKGROUND OF THE INVENTION

Manual respiration bags are used for the manual positive pressure respiration (ventilation) of patients in the area of intensive care and neonatal intensive care to maintain ventilation. The compression of the manual respiration bag causes an increase in the pressure in the respiration bag and a resulting breathing gas flow in the direction of the patient. The breathing volume thus administered as well as the respiration pressure necessary for this depend on the characteristics of the lungs and the respiratory tract of the particular patient. The manual respiration bags currently in use have as the safety means a pressure relief valve, which opens when a predetermined pressure is reached and this limits the respiration pressure.

The known respiration bags are also used to respirate or ventilate premature babies. It appears from numerous publications that the cause of the overinflation of the lung is not the respiration pressure but the tidal volume administered. A sufficient monitoring system is frequently unavailable to the user in conjunction with the manual respiration precisely for the respiration of premature babies. The pressure relief valve at the manual respiration bag also limits only the maximum pressure, but it does not control the tidal volume.

A respirator for the controlled mechanical respiration of patients, in which a volume-measuring means is provided between a respiration bag and a patient connection, is known from DE 195 28 113 C2. The prior-art respirator is used to recognize respiratory tract obstructions. Time constants of sections of the function are calculated and evaluated for this purpose in an evaluating means from an expiratory volume-flow function. However, the prior-art respirator contains no means for limiting the tidal volume supplied to the patient.

SUMMARY OF THE INVENTION

The basic object of the present invention is to provide a device and a process for the accurate metering of the tidal volume during manual respiration.

According to the invention, a respirator is provided with a tidal volume-measuring device for measuring a tidal volume V(t) between a respiration bag and a patient adapter. A first pressure-measuring device with a measured pressure value $p_1$ and a breathing gas interrupter is provided in series sequence between the patient adapter and the tidal volume-measuring device. A second pressure-measuring device measures a measured pressure value $p_2$ between the tidal volume-measuring device and the respiration bag. A control unit is connected with the tidal volume-measuring device and the pressure-measuring device. The control unit switches the breathing gas interruptor to the closed position when a predetermined tidal volume, $V(t)=V_{set}$, is reached, and switches out of the closed position when the difference between $p_1$ and $p_2$ ($p_2$ minus $p_1$) drops below zero.

According to another aspect of the invention, a process is provided for metering a predetermined tidal volume using a respiration bag, which is connected with a patient adapter via a tidal volume-measuring device. The process includes interrupting the breathing gas supply from the respiration bag with a breathing gas interrupter, which is arranged between the tidal volume-measuring device and the patient adapter, when a measured tidal volume V(t) has reached a predetermined tidal volume $V_{set}$. A first measured pressure value $p_1$ is determined at a first measuring point between the breathing gas interrupter and the patient adapter. A second measured pressure value $p_2$ is determined at a second measuring point between the tidal volume-measuring device and the respiration bag. The breathing gas interrupter is switched to the closed position when the difference $p_2$ minus $p_1$ is less than zero.

The tidal volume supplied to the patient is automatically limited with the respirator according to the present invention without the actuation of the manual respiration bag being limited or hindered. When the respiration bag is compressed, the breathing gas supply to the patient is automatically interrupted when the predetermined tidal volume is reached. The breathing gas flow to the patient is switched off in this case with a breathing gas interrupter. When the respiration bag is released, it is recognized by the comparison of two measured pressure values that the respiration bag must be filled with breathing air, and the breathing gas interrupter is opened in order to draw in air from the environment via the fresh gas valve located at the patient adapter. A sufficient breathing gas reservoir is thus again available in the respiration bag for the next inspiration stroke. During the refilling of the respiration bag, the patient can release the gas breathed in to the environment via an expiration valve at the patient adapter.

Together with a control unit, the breathing gas interrupter, the tidal volume-measuring device and the pressure-measuring means are advantageously accommodated in a housing, wherein the housing can be connected with both the respiration bag and the patient adapter via plug-type connections. The housing with the measuring and monitoring means can thus be inserted in an especially simple manner between an already existing respiration bag and a patient adapter. The housing also contains a power supply unit in the form of a battery or a low-voltage power pack, so that the unit can be used both stationarily and during transportation within the hospital.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The only FIGURE is a schematic view of a respirator/ventilator.

DESCRIPTION OF THE PREFERRED EMBODIMENTS

The only FIGURE shows a respirator 1, which comprises a series sequence of a patient adapter 2 with a mask 3, a first pressure-measuring means 4, a breathing gas interruptor 5, a tidal volume-measuring device 6, a second pressure-measuring means 7 and a respiration bag 8. The breathing gas interrupter 5, the pressure-measuring means 4, 7 and the tidal volume-measuring device 6 are connected to a control unit 20 and arranged in a common housing 9. The gas connection between the patient adapter 2 and the respiration bag 8 is established via plug-type connections 10, 11. A pressure relief valve 12 at the respiration bag 8 limits the respiration pressure to 45 mbar.

Ambient air is drawn in in the direction of arrow 14 via a fresh gas valve 13 at the patient adapter 2 in order for the respiration bag 8 to be able to be filled with breathing gas.

The breathing gas flows in the direction of arrow 15 via an inspiration valve 16 into the breathing mask 3 during the phase of inspiration, when the respiration bag 8 is compressed by a user, not shown in the figure. The inspiration valve 16 is closed during the expiration phase, and the expiration takes place via an expiration valve 17 in the direction of arrow 18. The respiration bag 8 is then again filled with breathing gas via the fresh gas valve 13. The expiration valve 17, which is controlled on the basis of the respiration pressure and is shown only schematically in the figure, is closed during the next inspiration stroke.

The respirator 1 according to the present invention operates as follows:

A set point for the tidal volume $V_{set}$ to be supplied is entered in the control unit 20 via an input keyboard 19 and stored there. When the respiration bag 8 is compressed, the breathing gas enters the mask 3 via the tidal volume-measuring device 6, the breathing gas interrupter 5 and the inspiration valve 16. The tidal volume V(t) is determined in the tidal volume-measuring device 6 by integrating the breathing gas flow. The instantaneous value V(t) is continuously compared with the set point $V_{set}$ in the control unit 20. At the same time, the instantaneous pressure $p_1$ is determined at the first measuring point with the first pressure-measuring means 4 and the instantaneous pressure $p_2$ is determined at a second measuring point with the second pressure-measuring means 7. The control unit 20 determines the pressure difference $\Delta p = p_2 - p_1$ from the measured pressure values $p_1$, $p_2$. Aside from brief, nonstationary changes in pressure, no pressure difference $\Delta p$ occurs normally during the inspiration phase, so that the pressure difference $\Delta p$ is zero. When the tidal volume V(t) reaches the set point $V_{set}$, V(t)= $V_{set}$, the breathing gas interruptor 5 is closed and the breathing gas supply is interrupted. When the respiration bag 8 is released, the measured pressure value $p_2$ drops below the measured pressure value $p_1$, so that the pressure difference $\Delta p = p_2 - p_1$ becomes negative. When a negative pressure difference is recognized in the control unit 20, the breathing gas interrupter 5 is opened, so that the respiration bag 8 can again be filled with ambient air via the fresh gas valve 13. At the same time, the expiration phase is initiated via the expiration valve 17. The respiration bag 8 filled with ambient air is now again ready for a new inspiration stroke.

While a specific embodiment of the invention has been shown and described in detail to illustrate the application of the principles of the invention, it will be understood that the invention may be embodied otherwise without departing from such principles.

What is claimed is:

1. A respirator comprising:
   a respiration bag;
   a patient adapter;
   a tidal volume-measuring device for measuring a tidal volume V(t) between said respiration bag and said patient adapter;
   a first pressure-measuring means for measuring a pressure value $p_1$ between the patient adapter and the tidal volume-measuring device;
   a breathing gas interrupter in series sequence with said first pressure-measuring means between said patient adapter and said tidal volume-measuring device;
   a second pressure-measuring means for measuring a pressure value $p_2$ between said tidal volume-measuring device and said respiration bag; and
   a control unit connected with the tidal volume-measuring device, said first pressure measuring means and said pressure-measuring means, said control unit switching said breathing gas interrupter to a closed position when a predetermined tidal volume, V(t)=$V_{set}$, is reached, and a switching said breathing gas interrupter out of the closed position when the difference between $p_2$ and $p_1$ drops below zero.

2. A respirator in accordance with claim 1, wherein said pressure-measuring means, said breathing gas interruptor and said tidal volume-measuring device are accommodated in a modular manner in a common housing, and plug connections are formed between said housing and said respiration bag and said housing and said patient adapter.

3. A process for metering a predetermined tidal volume with a respiration bag connected with a patient adapter via a tidal volume-measuring device, the process comprising the steps of:
   interrupting the breathing gas supply from the respiration bag with a breathing gas interrupter, which is arranged between the tidal volume-measuring device and the patient adapter, when a measured tidal volume V(t) has reached a predetermined tidal volume $V_{set}$;
   determining a first measured pressure value $p_1$ at a first measuring point between the breathing gas interruptor and the patient adapter and determining a second measured pressure value $p_2$ at a second measuring point between the tidal volume-measuring device and the respiration bag; and
   switching of the breathing gas interrupter to a closed position when the difference $p_2$ minus $p_1$ is less than zero.

* * * * *